United States Patent
Qu et al.

(10) Patent No.: US 10,429,483 B2
(45) Date of Patent: Oct. 1, 2019

(54) INTERNAL INTEGRATED CIRCUIT RESISTANCE CALIBRATION

(71) Applicant: Analog Devices Global, Hamilton (BM)

(72) Inventors: GuangYang Qu, Beijing (CN); Leicheng Chen, Rongjiang Town (CN); Michael Looney, Croagh (IE)

(73) Assignee: Analog Devices Global, Hamilton (BM)

( * ) Notice: Subject to any disclaimer, the term of this patent is extended or adjusted under 35 U.S.C. 154(b) by 365 days.

(21) Appl. No.: 15/586,877

(22) Filed: May 4, 2017

(65) Prior Publication Data

US 2018/0321349 A1 Nov. 8, 2018

(51) Int. Cl.
*G01R 35/00* (2006.01)
*G01R 27/14* (2006.01)

(52) U.S. Cl.
CPC .......... *G01R 35/005* (2013.01); *G01R 27/14* (2013.01)

(58) Field of Classification Search
CPC ........ G01R 17/02; G01R 27/00; G01R 27/08; G01R 27/14; G01R 27/16; G01R 35/00; G01R 35/005; G01K 15/00; G01K 15/002
See application file for complete search history.

(56) References Cited

U.S. PATENT DOCUMENTS

| | | | |
|---|---|---|---|
| 4,968,946 A | 11/1990 | Maier | |
| 5,469,071 A * | 11/1995 | Obata | G01K 7/206 324/691 |
| 6,452,405 B1 | 9/2002 | Collier-Hallman | |
| 2006/0263254 A1 | 11/2006 | Lee | |
| 2012/0065540 A1 | 3/2012 | Yarden et al. | |
| 2013/0102061 A1 * | 4/2013 | Coursey | G01K 7/20 435/286.1 |
| 2018/0164356 A1 * | 6/2018 | Yang | G01R 27/14 |
| 2018/0284011 A1 * | 10/2018 | Farkas | G01R 17/02 |

FOREIGN PATENT DOCUMENTS

EP 1262755 A1 12/2002

OTHER PUBLICATIONS

"Analog Devices ADuDM350 Hardware Reference Manual UG-587", Rev. C, © 2014-2016, (2014-2016), 459 pgs.
"Analogy Devices 16-Bit Precision, Low Power Metter On A Chip with Cortex-M3 and Connectivity", © 2014 Analogy Devices, Inc., Data Sheet ADuCM350 Rev. A, (2014), 41 pgs.
"Designing a PotentioStatic Cicuit", Alphasense Application Note—AAN 105-03, (Mar. 2009), 5 pgs.

* cited by examiner

*Primary Examiner* — Son T Le
(74) *Attorney, Agent, or Firm* — Schwegman Lundberg & Woessner, P.A.

(57) ABSTRACT

The sensor interface IC measures or calibrates a target resistance to be used as a gain resistor for a TIA amplifier in the sensor interface IC. One or more excitation currents are generated in response to different specified excitation voltages that are applied to an external calibration resistor having a specified calibration resistance value. Response voltages are measured across the target resistor, respectively in response to the corresponding different one or more excitation currents. The resistance value of the target resistor is determined using a difference between the measured response voltages, a difference between the specified excitation voltages, and the specified calibration resistance value.

20 Claims, 6 Drawing Sheets

INTERNAL INTEGRATED CIRCUIT RESISTANCE CALIBRATION

FIELD OF THE DISCLOSURE

This document pertains generally, but not by way of limitation, to the field of integrated circuits and, in particular, to calibrating internal integrated circuit resistances.

BACKGROUND

In order to reduce the size of circuits, circuit components may be reduced in size in order to fit the circuit on an integrated circuit. This can result in inaccurate component values for the circuit. For example, the resistance values of integrated resistors may not be not as accurate as resistance values of external resistors in which the resistance can be more accurately selected for desired circuit performance. However, this defeats the purpose of trying to reduce the size of the circuit by integrating the components.

SUMMARY OF THE DISCLOSURE

The inventors have recognized, among other things, a need for measuring and calibrating internal load and feedback resistances while a sensor is coupled to a sensor integrated circuit.

One example includes a method of measuring an integrated circuit (IC) resistance value of a target resistor using an excitation current that is subject to reduction by an external sensor leakage current or other leakage current before reaching the target resistor. The method includes generating different first and second excitation currents in response to different first and second specified excitation voltages applied to a calibration resistor having a specified calibration resistance value. Different first and second response voltages are measured across the target resistor, respectively in response to the corresponding different first and second excitation currents. The integrated circuit resistance value of the target resistor is determined using a difference between the measured first and second response voltages, a difference between the first and second specified excitation voltages, and the specified calibration resistance value.

Another example includes a sensor interface integrated circuit (IC) for measuring a resistance value of a target resistor using an excitation current that is subject to reduction by an external sensor leakage current of a sensor coupled to the IC. The sensor interface IC includes a current sensor circuit, including at least one target resistor for sensing the response current produced by the sensor. A resistance value measurement circuit is coupled to the target resistor to measure a resistance value of the target resistor. The resistance value measurement circuit includes a voltage excitation circuit to apply one or more specified excitation voltages to a calibration resistor having a specified calibration resistance value to generate, in response, a different respective excitation current for each specified excitation voltage. A voltage measurement circuit measures a different respective response voltage across the target resistor respectively in response to each corresponding different excitation current. A computation circuit determines the resistance value of the target resistor using a difference between the measured different respective response voltages, a difference between the one or more specified excitation voltages, and the specified calibration resistance value.

Yet another example includes a sensor interface integrated circuit (IC) for measuring or calibrating a resistance value of a target resistor using an excitation current that is subject to reduction by an external sensor leakage current of a sensor coupled to the IC. The sensor interface IC includes a current sensor circuit with at least one target resistor for sensing the response current produced by the sensor. A resistance value measurement or calibration circuit is coupled to the target resistor to measure or calibrate a resistance value of the target resistor. The resistance value measurement or calibration circuit includes a current excitation circuit to apply one or more specified excitation currents through a calibration resistor having a specified calibration resistance value. A voltage measurement circuit measures a different respective response voltage across the target resistor respectively in response to each corresponding different excitation current. A computation circuit determines the resistance value of the target resistor using a difference between the measured different respective response voltages, a difference between the one or more specified excitation currents, and the specified calibration resistance value.

This section is intended to provide an overview of the subject matter of the present patent application. It is not intended to provide an exclusive or exhaustive explanation of the invention. The detailed description is included to provide further information.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

A sensor system can include a sensor (e.g., gas sensor) coupled to a sensor interface integrated circuit (IC). The sensor may be used to detect not only the presence of a gas but also the concentration of the gas. The sensor may encompass various types of sensors such as photoionization, infrared, electrochemical or semiconductor.

Electro-chemical sensors detect gases by a chemical reaction that takes place when the monitored gas is diffused into the sensor, through the back of the porous membrane to the working electrode where it is oxidized or reduced. This electrochemical reaction results in an electric current that passes through an external circuit. In addition to measuring, amplifying and performing other signal processing functions, the external circuit maintains the voltage across the sensor between the working and counter electrodes for a two electrode sensor or between the working and reference electrodes for a three electrode cell. At the counter electrode an equal and opposite reaction occurs, such that if the working electrode is an oxidation, then the counter electrode is a reduction. Semiconductor sensors are commonly used to detect hydrogen, oxygen, alcohol vapor, and harmful gases such as carbon monoxide.

The sensor interface IC is responsible for measuring the change in current of the sensor in order to determine the presence and concentration of the monitored gas. The sensor IC can then output a representation of the presence and concentration of the monitored gas in either a digital or analog format for display or some other alerting means.

The sensor IC includes a direct current (DC) measurement circuit for measuring the sensor resistance to determine the presence and concentration of the gas. The sensor IC also uses an alternating current (AC) measurement circuit for measuring an impedance of the sensor in order to monitor the health of the sensor itself.

A load resistance (e.g., resistor $R_{LOAD}$) and a transimpedance amplifier (TIA) resistance (e.g., resistor $R_{TIA}$) are part of the DC measurement circuit. The load resistance $R_{LOAD}$ may be used as a load for the sensor for current stability. The TIA resistance $R_{TIA}$ may be used as a feedback gain resistor for a TIA amplifier and to convert the sensor current into a voltage signal. Both resistors are described subsequently in greater detail.

Some sensor ICs use load and TIA gain resistors that are external to the sensor IC. In order to reduce the size of the sensor circuitry, $R_{LOAD}$ and $R_{TIA}$ may be integrated onto the IC. The integrated resistors are not as accurate as the external resistors and, thus, it would be desirable to measure or calibrate one or more of these resistors to attempt to achieve greater accuracy in sensor measurements.

Figure 1:
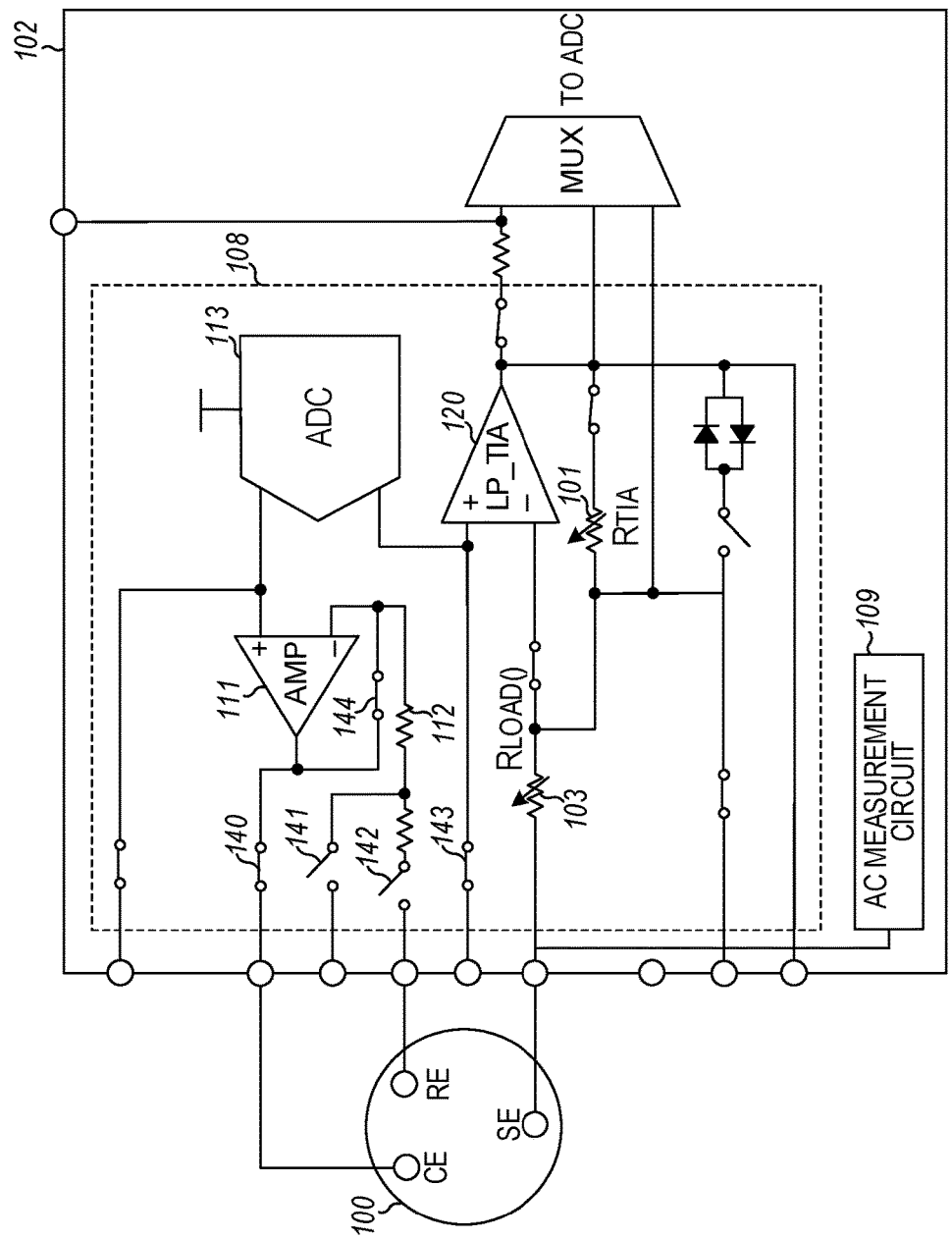
FIG. 1 is a schematic diagram of a sensor system, such as in accordance with various embodiments.

FIG. 1 is a schematic diagram of an example of a sensor system, such as in accordance with various embodiments. The system includes the sensor 100 and the sensor IC 102. The sensor IC 102 includes a DC measurement circuit 108 and an AC measurement circuit 109. The DC measurement circuit 108 includes an amplifier 111, an amplifier gain resistance 112, an analog-to-digital converter (ADC) 113, the $R_{LOAD}$ resistor, the $R_{TIA}$ resistor 101, a TIA amplifier 120, and a plurality of switches 140-144.

For purposes of clarity and brevity, not all of the components of the sensor IC 102 are shown or described. Only those components relevant to the structure and operation of the internal integrated resistance calibration are described.

Depending on the type of sensor, the sensor 100 may include a reference electrode (RE), a counter electrode (CE), and a sensor electrode (SE). For example, the reference electrode may be used by the sensor IC 102 to maintain a fixed potential at the sensing electrode during a sensing operation. The counter electrode completes the circuit with the sensing electrode by reducing some chemical species if the sensing electrode is oxidizing. The potential of the counter electrode may be allowed to float and change as the gas concentration changes. The potential on the counter electrode may not be important as long as the sensor IC 102 can provide sufficient voltage and current to maintain the sensing electrode at the same potential as the reference electrode. The biasing and measurements of the sensor 100 are controlled by the state of the plurality of switches 140-144.

The DC measurement circuit 108 is coupled to the sensor 100 and is used to measure sensor signals provided by the sensor 100. The AC measurement circuit 109 is coupled to the sensor 100 and is used to measure the health of the sensor 100 by measuring the impedance of the sensor 100.

The ADC 113 is coupled to the amplifier 111 and provides an analog voltage to the positive input of the amplifier 111 that has at least one gain resistor 112. The output of the amplifier 111 is coupled to the counter electrode of the sensor 100 to provide an operational voltage to the sensor 100. The reference electrode is coupled through the gain resistor 112 to the inverting (e.g., negative) input of the amplifier 111. The sensing electrode of the sensor 100 is coupled to the TIA amplifier 120 through the load resistor 103. The gain resistor 101 for the TIA amplifier 120 and has resistance value of $R_{TIA}$.

The $R_{TIA}$ and $R_{LOAD}$ resistances 101, 103 are shown integrated into the sensor IC 102. While the size of a circuit comprising the sensor IC and external resistors is reduced by integrating the TIA gain and load resistors 101, 103, the integrated resistances are typically not as accurate as an external resistor and should be calibrated for accurate operation of the sensor and sensor IC.

Figure 2:
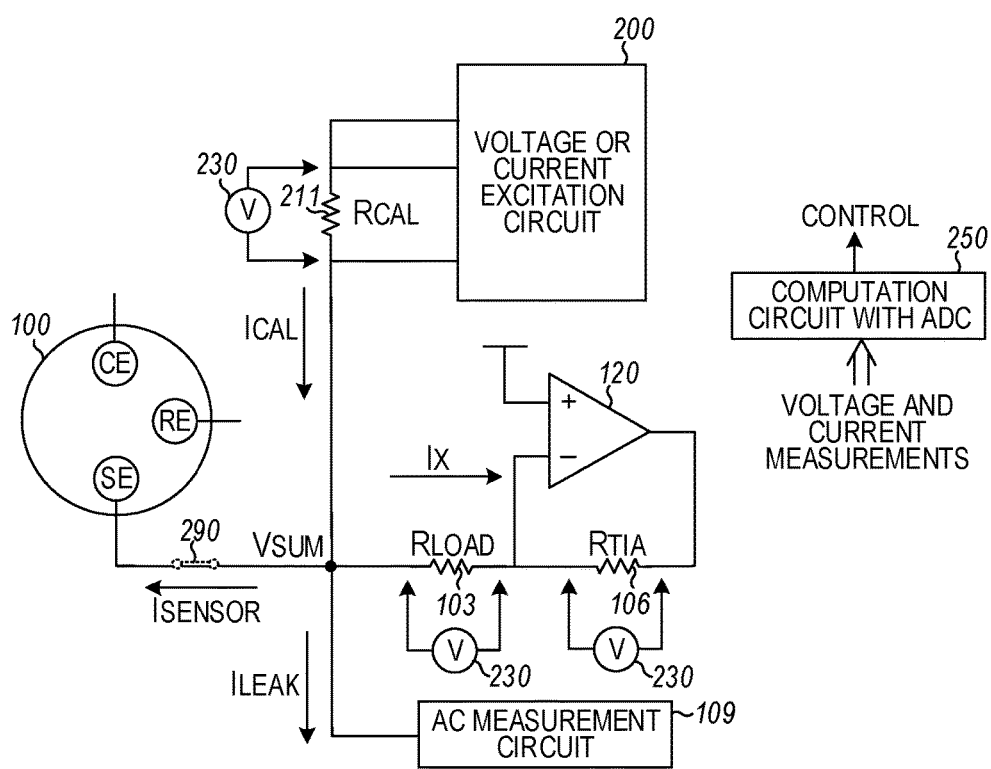
FIG. 2 is an operational block diagram of the sensor system for internal resistance calibration, such as in accordance with various embodiments.

FIG. 2 is an operational block diagram of the sensor system for internal resistance calibration, such as in accordance with various embodiments. The system of FIG. 2 may also be referred to as a resistance value measurement or calibration circuit. The system includes a voltage or current excitation circuit 200, a TIA amplifier 120, a calibration resistor 211, a sensor 100, an optional switch 290, an AC measurement circuit 109, an RLOAD resistor 103, an RTIA resistor 106, and a computation circuit with an ADC 250.

In order to calibrate the internal resistances $R_{TIA}$ and $R_{LOAD}$ 101, 103, a calibration current $I_{CAL}$ is generated through an external calibration resistor 211, having resistance $R_{CAL}$, by application of an excitation voltage generated by the voltage excitation circuit 200. In another embodiment, block 200 is a current excitation circuit. A problem with calibrating the internal $R_{TIA}$ and $R_{LOAD}$ resistances 101, 103 is that, while the sensor 100 is coupled to the sensor IC 102, a sensor current $I_{SENSOR}$ to the sensor 100 reduces $I_{CAL}$ so that $I_X$ through the resistors 101, 103 is not equal to $I_{CAL}$. This results in errors in measuring voltages across the resistors 101, 103 and, thus, determining the $R_{TIA}$ and $R_{LOAD}$ resistance values. Additionally, a relatively small (e.g., <0.1%) leakage current $I_{LEAK}$ to other blocks (e.g., AC measurement circuit 109) similarly reduces $I_{CAL}$. Switches need not be used in series with the sensor 100 to remove the sensor during calibration due to the relatively small (e.g., 0-100 Ohms (Ω) value of the $R_{LOAD}$ resistance 103 and a relatively high (e.g., 5 kΩ) switching resistance. The inventors have determined a method for calibrating and measuring resistances $R_{CAL}$ and $R_{LOAD}$ 101, 103 while the sensor 100 remains connected to the sensor IC 102.

Figure 3:
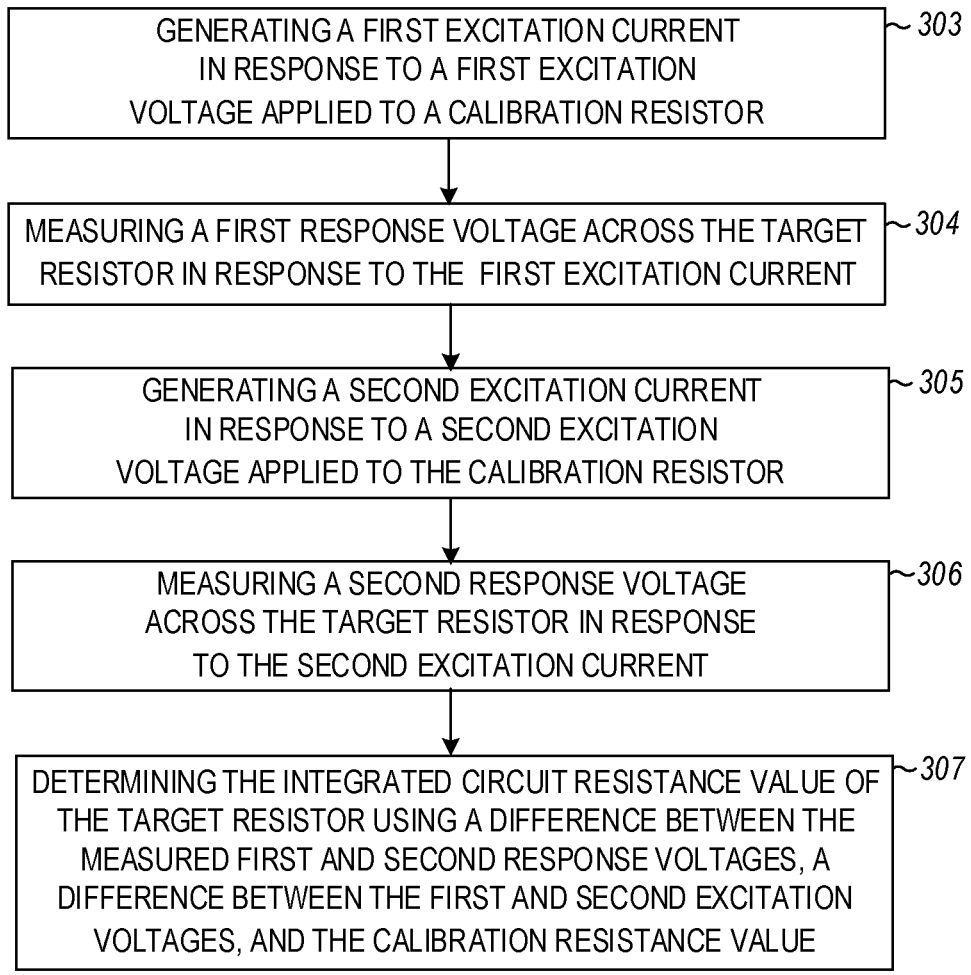
FIG. 3 is a flowchart of an embodiment of a method for internal integrated circuit resistance calibration, such as in accordance with various embodiments.

FIG. 3 is a flowchart of an embodiment of a method for internal integrated circuit resistance calibration, such as in accordance with various embodiments. In discussing the method of FIG. 3, reference is also made to the operational block diagram of FIG. 2. The method of FIG. 3 illustrates the DC measurements performed in calibrating the resistances of the internal resistors 101, 103.

In block 303, different first and second excitation currents ($I_{CAL1}$ and $I_{CAL2}$) are generated in response to different first and second excitation voltages ($V_{X1}$ and $V_{X2}$) applied to the calibration resistor 211. The voltage excitation circuit 200 generates the first and second excitation voltages applied across the calibration resistor 211 having resistance $R_{CAL}$. For purposes of illustration only, the first excitation voltage $V_{X1}$ may be 10 mV and the second excitation voltage $V_{X2}$ may be 20 mV. Other embodiments may use other voltages or more than two voltages. In still other embodiments, instead of using excitation voltages, one or more excitation currents may be generated through the calibration resistor 211.

The calibration resistor 211 is external to the sensor IC 102. The value of $R_{CAL}$ may be any known resistance value since it is used to determine first and second $I_{CAL}$ currents through the calibration resistor 211 as respectively generated by the first and second excitation voltages.

The calibration current $I_{CAL}$ may be expressed as:

$$I_{CAL} = I_X + I_{SENSOR} + I_{LEAK},$$

where $I_X$ is the current through the one or more target resistors to be calibrated, $I_{SENSOR}$ is the sensor current, and $I_{LEAK}$ is the leakage current caused by other blocks of the sensor IC. Using Ohm's Law, this equation for $I_{CAL}$ may also be expressed as:

$$\frac{V_{exc}}{R_{CAL}} = \frac{V_X}{R_X} + I_{SENSOR} + I_{LEAK}$$

where $V_{exc}$ represents the excitation voltage across $R_{CAL}$, $V_X$ represents the response voltage measured across either one of the target resistors 101, 103 as a result of the corresponding current $I_X$, and $R_X$ represents one of either the $R_{LOAD}$ resistance 103 or the $R_{TIA}$ resistance 101. The resistance value of $R_X$ may then be expressed as:

$$R_X = \frac{1}{1 - \frac{R_{CAL} \cdot I_{SENSOR}}{V_{exc}} - \frac{R_{CAL} \cdot I_{LEAK}}{V_{exc}}} \cdot \frac{V_X}{V_{exc}} \cdot R_{CAL}$$

The first term of this equation may be ignored due to the relatively large values of $I_{SENSOR}$ and $I_{LEAK}$ so that determining $R_X$ may be accomplished by:

$$R_X = \frac{V_X}{V_{exc}} \cdot R_{CAL}$$

In block 305 of FIG. 3, the different first and second response voltages ($V_{X1}$ and $V_{X2}$) are measured across the target resistor ($R_X$) respectively in response to the corresponding different first and second excitation currents ($I_{X1}$ and $I_{X2}$). The voltage measurements may be made by on-chip voltage measurement circuits 230 (e.g., ADC). The voltage, current, or resistance measurements may be input to a computation circuit 250 (e.g., including the ADC) for performing the calculations herein. By exciting two or more voltages, the sensor current and leakage current can be eliminated:

$$I_{CAL1} = I_{X1} + I_{SENSOR} + I_{LEAK}$$

$$I_{CAL2} = I_{X2} + I_{SENSOR} + I_{LEAK}$$

When the $I_{CAL1}$ and $I_{CAL2}$ measurements are subtracted:

$$\Delta I_{CAL} = \Delta I_X$$

$$\frac{\Delta V_{CAL}}{R_{CAL}} = \Delta I_{CAL} = \Delta I_X = \frac{\Delta V_X}{R_X}$$

$$R_X = \frac{\Delta V_X}{\Delta V_{exc}} \cdot R_{CAL}.$$

Thus, from the above, it can be seen that the resistance value of the target resistor ($R_X$) is determined by using a difference between the measured first and second response voltages ($\Delta V_X$), a difference between the first and second excitation voltages ($\Delta V_{exc}$) or one or more excitation currents, and the calibration resistance value $R_{CAL}$, as seen in block 307 of FIG. 3. This value of $R_X$ can then be used in adjusting the integrated resistance value of the target resistor using the determined integrated resistance value of the target resistor. The adjusted resistance value can then be used as either the $R_{LOAD}$ or the $R_{TIA}$ resistance values during sensor measurements.

Generally, the sensor current $I_{SENSOR}$ is associated with a gas concentration and is not likely to change in the time that the plurality of DC measurements are being made to determine the $R_X$ value. However, in another embodiment, a possible change in $I_{SENSOR}$ can be taken into account by performing an AC measurement.

During the AC measurement, the $I_{SENSOR}$ and $I_{LEAK}$ currents disappear at a specific frequency. The specific frequency may be determined by empirical experimentation with the sensor or known characteristics of the sensor. Thus, the first and second excitation voltages can include first and second frequencies. The voltages across resistors $R_{LOAD}$ and $R_{TIA}$ are measured. These voltages will have two components: one is correlated to an excitation frequency and the other is correlated to the sensor current. However, the spectrum of energy is different at different frequencies. Thus, a Fast Fourier Transform (FFT) bandpass filter may be used to extract the measured voltage at the specific frequency. With the known voltage and known current, the resistance value of the target resistor can be determined using Ohm's Law.

In the above-described embodiment, the sensor 100 is connected to sensor interface IC 102 without a switch. In another embodiment, the sensor 100 may be coupled to the sensor interface IC 102 through an optional switch 290. In this embodiment, the sensor 100 can be removed from being coupled to the sensor interface IC 102 during any measurements for determining the target resistor resistance by opening the switch 290.

Referring to FIG. 2, it can be seen that during the calibration operation, the CE and RE electrodes of the sensor 100 are floating. The sensor 100 acts as a capacitor with a relatively large capacitance. Variations in a summing node voltage $V_{SUM}$ (e.g., voltage sensing node) may cause the sensor capacitance to discharge to the sensor IC, thus causing a current to flow as $I_{SENSOR}$. As described previously, any $I_{SENSOR}$ current is undesirable due to the inaccuracies caused in calibrating either $R_{LOAD}$ or $R_{TIA}$. Thus, it would be desirable to keep the $V_{SUM}$ voltage from changing due to different sensors being coupled to the sensor IC having different characteristics. The embodiment illustrated in FIGS. 4-7 can be used to calibrate $R_{LOAD}$ or $R_{TIA}$ to account for the different sensors and their respective characteristics.

Figure 4:
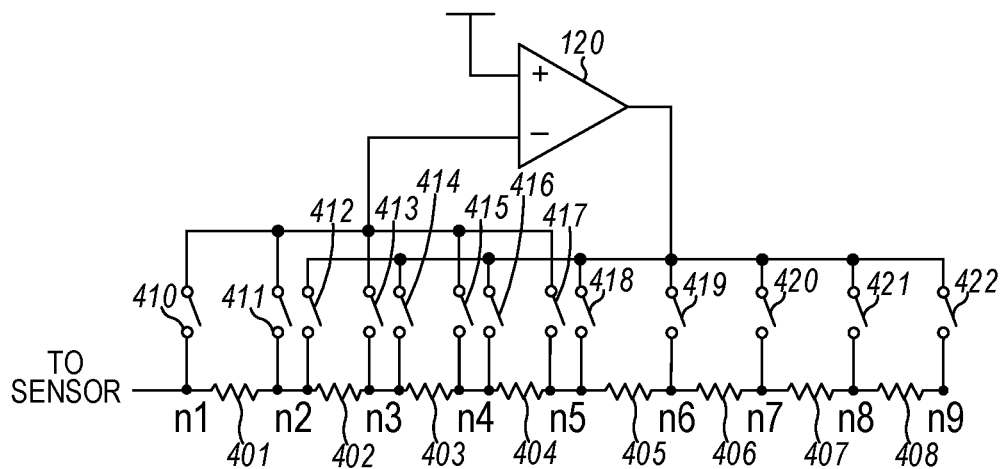
FIG. 4 is a schematic diagram of a configurable $R_{LOAD}$ and $R_{TIA}$ architecture, such as in accordance with various embodiments.

FIG. 4 is a schematic diagram of a configurable $R_{LOAD}$ and $R_{TIA}$ architecture, such as in accordance with various embodiments. This architecture is part of the resistance value measurement and calibration circuit.

The architecture includes a plurality of resistors 401-408 (e.g., network of resistors) and a plurality of switches 410-422 to switchably couple the network of resistors to the TIA amplifier 120. While the resistance of the switch may cause problems, as described previously, when placed between the $R_{LOAD}$ or $R_{TIA}$ and the sensor, no such problem exists when placing the switch between the resistors and the amplifier 120. The switches 410-422 may be implemented in various ways such as with transistors such that when a switch is closed the transistor is activated and when the switch is open, the transistor is deactivated.

The network of resistors is divided into two groups of resistors. The first group of resistors is switchably coupleable between the inverting input of the TIA amplifier 120 and the sensor. The second group of resistors is switchably coupleable between the output of the TIA amplifier 120 and the inverting input of the TIA amplifier 120.

Each adjacent pair of resistors is coupled together by a node N1-N9. At least one switch is coupled to a respective node and at least one of the inverting input of the amplifier 120 or the output of the amplifier 120. For example, switches 410, 411, 413, 415, 417 are coupled between their respective node and the inverting input of the amplifier 120. Similarly, switches 412, 414, 416, 418-422 are coupled between their respective node and the output of the amplifier 120. The switches are controlled by the control output of the computation circuit 250.

In order to keep $V_{SUM}$ from changing, $R_{LOAD}$ is set to a resistance of zero ohms so that the $V_{SUM}$ node is connected directly to the inverting input of the amplifier 120. However, before setting $R_{LOAD}$ to zero ohms, $R_{TIA}$ should first be determined so that the proper ratio between $R_{LOAD}$ and $R_{TIA}$ is established. An accurate $R_{TIA}$ is necessary in order for accurate conversion of $I_{CAL}$ current signal to the $V_X$ voltage signal. This is accomplished by setting the switches to alter the $R_{LOAD}$ and $R_{TIA}$ resistance values as follows in order to vary a resistance value of the first resistor component $R_{LOAD}$ relative to a resistance value of the second resistance component $R_{TIA}$.

Figure 5:
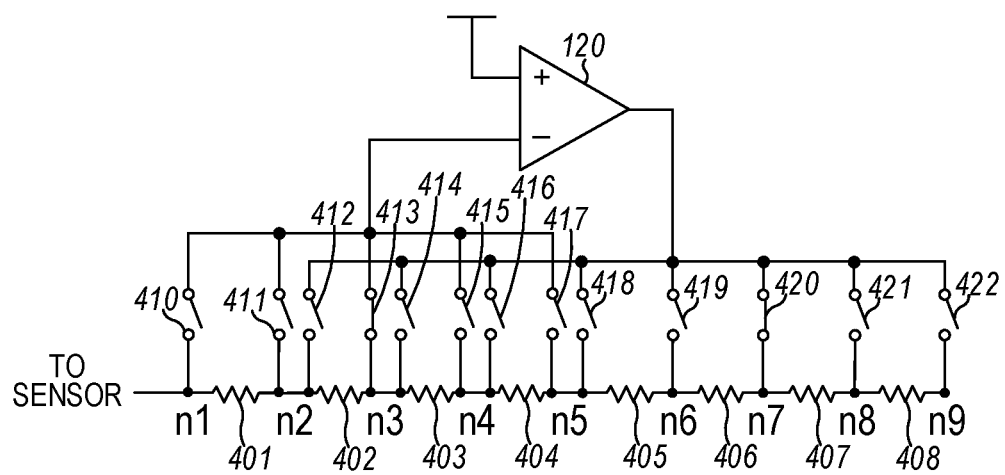
FIG. 5 is a schematic diagram of the configurable $R_{LOAD}$ and $R_{TIA}$ architecture in an example initial configuration of a nominal operating mode, such as in accordance with various embodiments.

FIG. 5 is a schematic diagram of the configurable $R_{LOAD}$ and $R_{TIA}$ architecture in an example initial configuration of a nominal operating mode, such as in accordance with various embodiments. The configuration of FIG. 5 is an example configuration in which $R_{LOAD}$ is set to some initial resistance by closing switch 413 and thus connecting the resistors 401 and 402 between node N1 and node N3 to the inverting input of the amplifier 120. Thus, $R_{LOAD}$ is now the sum of these two resistors 401, 402. $R_{TIA}$ is set by closing switch 420 so that the total of the resistors between node N3 and node N7 is the resistance for $R_{TIA}$. The initial resistance values for $R_{LOAD}$ and $R_{TIA}$ are determined based on the sensor characteristics and the sensor's requirements for $R_{LOAD}$ and $R_{TIA}$.

Figure 6:
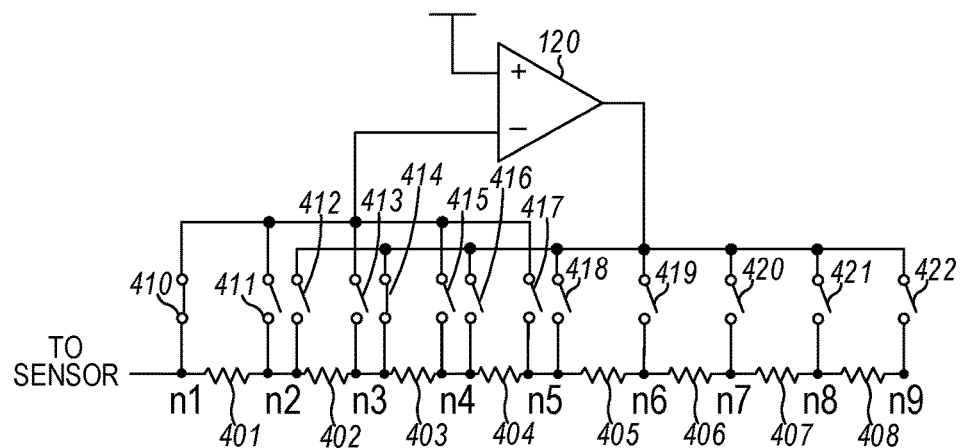
FIG. 6 is a schematic diagram of the configurable $R_{LOAD}$ and $R_{TIA}$ architecture in another example configuration to measure $R_{LOAD}$ from the embodiment of FIG. 5, such as in accordance with various embodiments.

FIG. 6 is a schematic diagram of the configurable $R_{LOAD}$ and $R_{TIA}$ architecture in another example configuration to measure $R_{LOAD}$ from the embodiment of FIG. 5, such as in accordance with various embodiments. This configuration bypasses $R_{LOAD}$ (e.g., set to zero ohms) so that the inverting input of the TIA amplifier 120 is connected directly to the $V_{SUM}$ node. Thus, $R_{TIA}$ is now equal to the previous resistance value for $R_{LOAD}$. This is accomplished by closing switch 410 to connect the amplifier inverting input directly to the $V_{SUM}$ node and closing switch 414 to connect resistors 401 and 402 between nodes N1 and N3 as $R_{TIA}$ which was the previous resistance value for $R_{LOAD}$. Since the new $R_{TIA}$ resistance is between the output and the inverting input of the TIA amplifier 120, the original $R_{LOAD}$ resistance value can be measured by measuring the differential voltage across the new $R_{TIA}$. This voltage differential is the $V_x$ in the above equation. Since the $V_{exc}$ and $R_{CAL}$ are known, resistance $R_X$ ($R_{LOAD}$) can now be computed. This resistance is temporarily set as $R_{TEMP1}$.

Figure 7:
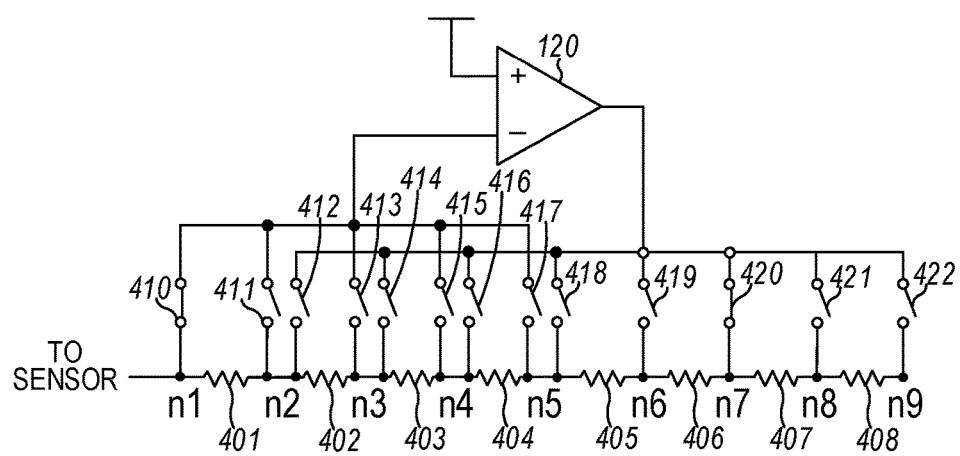
FIG. 7 is a schematic diagram of the configurable $R_{LOAD}$ and $R_{TIA}$ architecture in another example configuration to measure $R_{LOAD}+R_{TIA}$ of FIG. 5, such as in accordance with various embodiments.

FIG. 7 is a schematic diagram of the configurable $R_{LOAD}$ and $R_{TIA}$ architecture in another example configuration to measure $R_{LOAD}+R_{TIA}$ of FIG. 5, such as in accordance with various embodiments. $R_{TIA}$ may now be set as the total resistance of the initial $R_{LOAD}$ plus the initial $R_{TIA}$. This may be represented by $R_{TEMP2}=R_{LOAD}+R_{TIA}$. This is accomplished as illustrated in FIG. 7 by bypassing $R_{LOAD}$ by closing switch 410 to connect the $V_{SUM}$ node directly to the inverting input of the amplifier 120 and, thus, making $R_{LOAD}$ zero ohms. Switch 420 is closed so that $R_{TIA}$ is connected to the output of the amplifier 120 and is the total of all of the resistors 401-406 between node N1 and node N7. A measurement can now be performed to measure this total resistance for $R_{TEMP2}$.

Thus, $R_{TIA}$ can be determined by subtracting $R_{TEMP1}$ from $R_{TEMP2}$ to remove $R_{LOAD}$ from the equation. This results in the determination of $R_{TIA}$. In other words, $R_{TIA}=R_{TEMP2}-R_{TEMP1}$.

Figure 8:
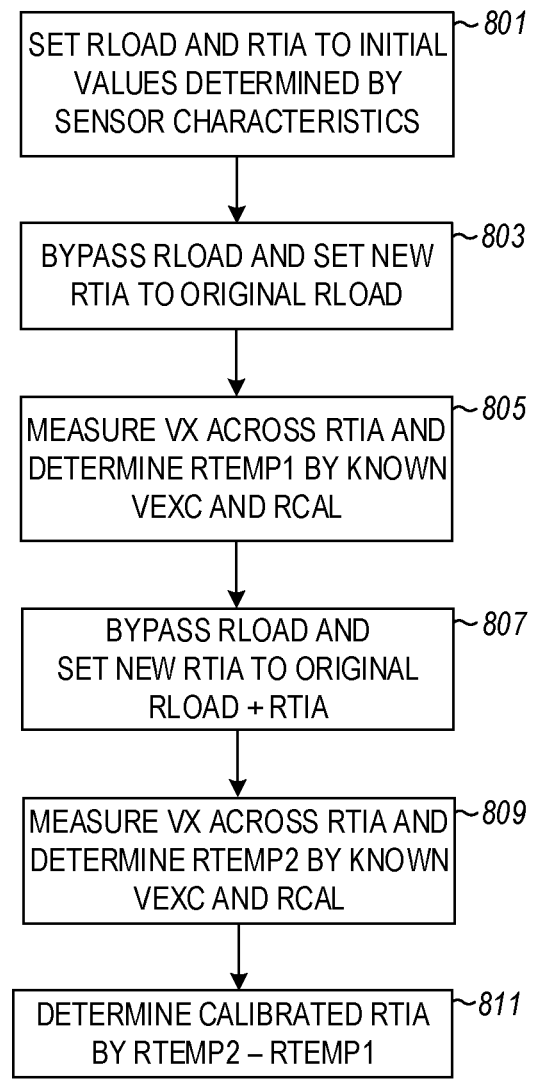
FIG. 8 is a flowchart of an embodiment of a method for internal integrated circuit resistance calibration, such as in accordance with various embodiments.

FIG. 8 is a flowchart of an embodiment of a method for internal integrated circuit resistance calibration, such as in accordance with various embodiments. In block 801, $R_{LOAD}$ and $R_{TIA}$ are set to initial values as determined by sensor characteristics. In block 803, $R_{LOAD}$ is bypassed so that it is set to zero ohms so that a new $R_{TIA}$ is set to the initial $R_{LOAD}$. In block 805, $V_X$ is measured across $R_{TIA}$ and, based on known $V_{exc}$ and $R_{CAL}$, $R_{TEMP1}$ can be determined from above $R_X$ equation (i.e., $$R_X = \frac{\Delta V_X}{\Delta V_{exc}} \cdot R_{CAL}\Big).$$

In block 807, $R_{LOAD}$ is bypassed and the new $R_{TIA}$ is set to the original $R_{LOAD}+R_{TIA}$ from the initial configuration. In block 809, $V_X$ is measured across $R_{TIA}$ and, based on known $V_{exc}$ and $R_{CAL}$, $R_{TEMP2}$ can be determined from above $R_X$ equation. In block 811, the calibrated $R_{TIA}$ can be determined by $R_{TEMP2}-R_{TEMP1}$ as the final value for the calibrated circuit.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. Method examples described herein can be machine or computer-implemented at least in part.

The above description is intended to be illustrative and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A method of measuring an integrated circuit (IC) resistance value of a target resistor using an excitation current that is subject to reduction by an external sensor leakage current or other leakage current before reaching the target resistor, the method comprising:
   generating different first and second excitation currents in response to different first and second specified excitation voltages applied to a calibration resistor having a specified calibration resistance value;
   measuring different first and second response voltages across the target resistor, respectively in response to the corresponding different first and second excitation currents; and
   determining the integrated circuit resistance value of the target resistor using a difference between the measured first and second response voltages, a difference between the first and second specified excitation voltages, and the specified calibration resistance value.

2. The method of claim 1, further comprising calibrating the integrated circuit resistance value of the target resistor, including adjusting the integrated circuit resistance value of the target resistor using the determined integrated circuit resistance value of the target resistor.

3. The method of claim 2, wherein calibrating the integrated circuit resistance value includes one or more further interactions of the generating, the measuring, and the determining.

4. The method of claim 1, wherein the first and second specified excitation voltages include one or more specified frequencies.

5. The method of claim 4, wherein the target resistor is coupled to a sensor external to the IC, wherein the one or more specified frequencies are higher than a nominal frequency response of the sensor to a parameter being sensed by the sensor.

6. The method of claim 4, wherein the target resistor includes a first resistor component, coupling a voltage sensing node to an amplifier input of an amplifier circuit, and a second resistor component feeding an amplifier output of the amplifier circuit to the amplifier input, the method further comprising varying a resistance value of the first resistor component relative to a resistance value of the second resistance component.

7. The method of claim 4, wherein a sensing electrode (SE) of the sensor is coupled to the target resistor, the method further comprising floating a reference electrode (RE) and a counter electrode (CE) of the sensor.

8. A sensor interface integrated circuit (IC) for measuring a resistance value of a target resistor using an excitation current that is subject to reduction by an external sensor leakage current of a sensor coupled to the IC, the sensor interface IC including:
   a current sensor circuit, including at least one target resistor for sensing the response current produced by the sensor; and
   a resistance value measurement circuit, coupled to the target resistor to measure a resistance value of the target resistor, the resistance value measurement circuit including:
      a voltage excitation circuit to apply one or more specified excitation voltages to a calibration resistor having a specified calibration resistance value to generate, in response, a different respective excitation current for each specified excitation voltage;
      a voltage measurement circuit to measure a different respective response voltage across the target resistor respectively in response to each corresponding different excitation current; and
      a computation circuit to determine the resistance value of the target resistor using a difference between the measured different respective response voltages, a difference between the one or more specified excitation voltages, and the specified calibration resistance value.

9. The sensor interface IC of claim 8, further comprising a sensor connected to the target resistor, wherein the sensor is external to the sensor interface IC.

10. The sensor interface IC of claim 9, wherein the sensor is further coupled to the calibration resistor.

11. The sensor interface IC of claim 8, wherein the voltage measurement circuit comprises an analog-to-digital converter to generate a digital representation of the measured respective response voltages for the computation circuit.

12. The sensor interface IC of claim 8, wherein the calibration resistor is coupled externally to the sensor interface IC.

13. The sensor interface IC of claim 8, wherein the computation circuit is configured to perform a direct current (DC) measurement and an alternating current (AC) measurement.

14. The sensor interface IC of claim 8, wherein a sensor is coupled to the target resistor through a switch that is open when the computation circuit determines the resistance value of the target resistor.

15. The sensor interface IC of claim 8, wherein the computation circuit is configured to determine the resistance value of the target resistor in response to $$R_X = \frac{\Delta V_X}{\Delta V_{exc}} \cdot R_{CAL}$$

where Rx is the resistance value of the target resistor, $\Delta V_X$ is the difference between the measured different respective responsive voltages, $\Delta V_{exc}$ is the difference between the one or more specified excitation voltages, and $R_{CAL}$ is the specified calibration resistance value.

16. A sensor interface integrated circuit (IC) for measuring or calibrating a resistance value of a target resistor using an excitation current that is subject to reduction by an external sensor leakage current of a sensor coupled to the IC, the sensor interface IC including:
  a current sensor circuit, including at least one target resistor for sensing the response current produced by the sensor; and
  a resistance value measurement or calibration circuit, coupled to the target resistor to measure or calibrate a resistance value of the target resistor, the resistance value measurement or calibration circuit including:
    a current excitation circuit to apply one or more specified excitation currents through a calibration resistor having a specified calibration resistance value;
    a voltage measurement circuit to measure a different respective response voltage across the target resistor respectively in response to each corresponding different excitation current; and
    a computation circuit to determine the resistance value of the target resistor using a difference between the measured different respective response voltages, a difference between the one or more specified excitation currents, and the specified calibration resistance value.

17. The sensor interface IC of claim 16, wherein the resistance value measurement or calibration circuit further comprises a network of resistors switchably coupled to an amplifier.

18. The sensor interface IC of claim 17, wherein the network of resistors comprises:
  a first group of resistors switchably coupleable between an inverting input of the amplifier and the sensor; and
  a second group of resistors switchably coupleable between an output of the amplifier and the inverting input.

19. The sensor interface IC of claim 18, wherein the computation circuit is configured to control switches that couple the network of resistors to the amplifier such that the sensor is connected to the inverting input and the output of the amplifier is coupled to the inverting input through a plurality of resistors.

20. The sensor interface IC of claim 19, wherein a total resistance of the plurality of resistors comprises the resistance value of the target resistor.

* * * * *